US008469993B2

(12) United States Patent
Rothberg et al.

(10) Patent No.: US 8,469,993 B2
(45) Date of Patent: Jun. 25, 2013

(54) ENDOSCOPIC INSTRUMENTS

(75) Inventors: Elliott Rothberg, Coral Springs, FL (US); William Gil De Montes, Pembroke Pines, FL (US); James M. Zardeskas, Pascoag, RI (US); David I. Freed, Westborough, MA (US); Michael J. Magill, Northboro, MA (US); Satish Sharma, Randolph, MA (US); Jon Gingrich, Shrewsbury, MA (US); Edward Boarini, Holliston, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1807 days.

(21) Appl. No.: 10/778,226

(22) Filed: Feb. 17, 2004

(65) Prior Publication Data
US 2004/0260198 A1 Dec. 23, 2004

Related U.S. Application Data

(60) Provisional application No. 60/479,145, filed on Jun. 18, 2003.

(51) Int. Cl.
*A61B 17/32* (2006.01)
*A61B 17/29* (2006.01)

(52) U.S. Cl.
USPC ............................. 606/207; 600/564

(58) Field of Classification Search
USPC ............... 604/22; 600/562–572; 606/120, 606/139–148, 157, 158, 167–180, 205–211, 606/151, 153; 433/4
See application file for complete search history.

(56) References Cited

U.S. PATENT DOCUMENTS

| 1,368,117 | A |   | 2/1921  | Claude            |         |
|-----------|---|---|---------|-------------------|---------|
| 1,387,781 | A |   | 8/1921  | King et al.       |         |
| 2,401,672 | A |   | 6/1946  | Tinnerman         |         |
| 2,668,538 | A | * | 2/1954  | Baker             | 606/207 |
| 3,050,578 | A |   | 8/1962  | Huebner           |         |
| 3,711,134 | A |   | 1/1973  | Goldberg          |         |
| 3,742,957 | A |   | 7/1973  | White             |         |
| 3,895,636 | A |   | 7/1975  | Schmidt           |         |
| 4,522,206 | A |   | 6/1985  | Whipple et al.    |         |
| 4,649,923 | A | * | 3/1987  | Hoffman           | 600/392 |
| 4,712,545 | A |   | 12/1987 | Honkanen          |         |
| 4,721,116 | A |   | 1/1988  | Schitngen et al.  |         |
| 4,763,668 | A |   | 8/1988  | Macek et al.      |         |
| 4,785,825 | A |   | 11/1988 | Romaniuk et al.   |         |
| 4,815,460 | A |   | 3/1989  | Porat et al.      |         |
| 4,815,476 | A |   | 3/1989  | Clossick          |         |

(Continued)

FOREIGN PATENT DOCUMENTS

AU  771184 B2   4/2001
CA  2 387 141 A1  4/2001

(Continued)

*Primary Examiner* — Kathleen Holwerda
(74) *Attorney, Agent, or Firm* — Bookoff McAndrews, PLLC

(57) ABSTRACT

Embodiments of the invention include a medical device with one or more of a variety of features. More particularly, embodiments of the invention relate to endoscopic devices that include one or more features that improve the use of the device. Examples of such features include chamfered edges and corners on, for example, the end effectors, a surface with a controlled finish also on, for example, the end effectors, a jaw with teeth and/or a tang having various configurations, a handle having soft-grip features, and/or an elongate member with varied rigidity.

15 Claims, 18 Drawing Sheets

U.S. PATENT DOCUMENTS

| | | | |
|---|---|---|---|
| 4,817,630 A | 4/1989 | Schitngen et al. | |
| 4,880,015 A | 11/1989 | Nierman | |
| 4,887,612 A | 12/1989 | Esser et al. | |
| 4,889,118 A | 12/1989 | Schwiegling | |
| 4,936,312 A * | 6/1990 | Tsukagoshi | 600/562 |
| 4,950,273 A | 8/1990 | Briggs | |
| 4,953,559 A | 9/1990 | Salerno | |
| 5,046,881 A | 9/1991 | Swager | |
| 5,052,402 A | 10/1991 | Bencini et al. | |
| 5,059,214 A * | 10/1991 | Akopov et al. | 606/207 |
| 5,082,000 A | 1/1992 | Picha et al. | |
| 5,133,727 A | 7/1992 | Bales et al. | |
| 5,133,735 A | 7/1992 | Slater et al. | |
| 5,133,736 A | 7/1992 | Bales, Jr. et al. | |
| 5,141,424 A | 8/1992 | Christof | |
| 5,141,519 A | 8/1992 | Smith et al. | |
| 5,152,778 A | 10/1992 | Bales, Jr. et al. | |
| 5,152,780 A | 10/1992 | Honkanen et al. | |
| 5,159,374 A | 10/1992 | Groshong | |
| 5,165,633 A | 11/1992 | Effa et al. | |
| 5,170,800 A | 12/1992 | Smith et al. | |
| 5,171,256 A | 12/1992 | Smith et al. | |
| 5,171,258 A | 12/1992 | Bales et al. | |
| 5,172,700 A | 12/1992 | Bencini et al. | |
| 5,174,300 A | 12/1992 | Bales et al. | |
| 5,176,702 A | 1/1993 | Bales et al. | |
| 5,178,624 A | 1/1993 | Kyun | |
| 5,192,298 A | 3/1993 | Smith et al. | |
| 5,203,785 A | 4/1993 | Slater | |
| 5,215,101 A | 6/1993 | Jacobs et al. | |
| 5,219,357 A | 6/1993 | Honkanen et al. | |
| 5,228,451 A | 7/1993 | Bales et al. | |
| 5,234,453 A | 8/1993 | Smith et al. | |
| 5,238,002 A * | 8/1993 | Devlin et al. | 600/564 |
| 5,241,968 A | 9/1993 | Slater | |
| 5,258,004 A | 11/1993 | Bales et al. | |
| 5,265,840 A | 11/1993 | Gillespie et al. | |
| 5,269,804 A | 12/1993 | Bales et al. | |
| 5,275,612 A | 1/1994 | Bales, Jr. | |
| 5,293,878 A | 3/1994 | Bales et al. | |
| 5,295,990 A | 3/1994 | Levin | |
| 5,300,087 A * | 4/1994 | Knoepfler | 606/207 |
| 5,304,203 A * | 4/1994 | El-Mallawany et al. | 606/207 |
| 5,312,400 A | 5/1994 | Bales et al. | |
| 5,313,935 A | 5/1994 | Kortenbach et al. | |
| 5,314,406 A | 5/1994 | Arias et al. | |
| 5,320,636 A | 6/1994 | Slater | |
| 5,330,502 A | 7/1994 | Hassler et al. | |
| 5,331,971 A | 7/1994 | Bales et al. | |
| 5,336,172 A | 8/1994 | Bales et al. | |
| 5,336,220 A | 8/1994 | Ryan et al. | |
| 5,342,390 A | 8/1994 | Slater et al. | |
| 5,350,356 A | 9/1994 | Bales et al. | |
| 5,359,993 A | 11/1994 | Slater et al. | |
| 5,373,854 A | 12/1994 | Kolozsi | |
| 5,374,277 A | 12/1994 | Hassler | |
| 5,389,104 A | 2/1995 | Hahnen et al. | |
| 5,392,789 A | 2/1995 | Slater et al. | |
| 5,394,885 A | 3/1995 | Francese | |
| 5,395,364 A | 3/1995 | Anderhub et al. | |
| 5,395,369 A | 3/1995 | McBrayer et al. | |
| 5,395,375 A | 3/1995 | Turkel et al. | |
| 5,395,396 A | 3/1995 | Lindgren et al. | |
| 5,396,900 A * | 3/1995 | Slater et al. | 600/564 |
| 5,419,339 A | 5/1995 | Palmer | |
| 5,429,596 A | 7/1995 | Arias et al. | |
| 5,431,645 A | 7/1995 | Smith et al. | |
| 5,439,378 A | 8/1995 | Damon | |
| 5,443,380 A | 8/1995 | Riehl | |
| 5,452,335 A | 9/1995 | Slater et al. | |
| 5,454,378 A | 10/1995 | Palmer et al. | |
| 5,462,546 A | 10/1995 | Rydell | |
| 5,482,054 A * | 1/1996 | Slater et al. | 600/564 |
| 5,507,296 A | 4/1996 | Bales et al. | |
| 5,507,297 A | 4/1996 | Slater et al. | |
| 5,531,755 A | 7/1996 | Smith et al. | |
| 5,542,432 A | 8/1996 | Slater et al. | |
| 5,549,547 A | 8/1996 | Cohen et al. | |
| 5,549,606 A | 8/1996 | McBrayer et al. | |
| 5,553,624 A * | 9/1996 | Francese et al. | 600/564 |
| 5,558,100 A | 9/1996 | Cox | |
| 5,562,102 A | 10/1996 | Taylor | |
| 5,569,243 A | 10/1996 | Kortenbach et al. | |
| 5,601,599 A * | 2/1997 | Nunez | 606/205 |
| 5,603,711 A | 2/1997 | Parins et al. | |
| 5,613,499 A * | 3/1997 | Palmer et al. | 600/564 |
| 5,636,639 A | 6/1997 | Turturro et al. | |
| 5,638,827 A | 6/1997 | Palmer et al. | |
| 5,645,075 A | 7/1997 | Palmer et al. | |
| 5,647,115 A | 7/1997 | Slater et al. | |
| 5,666,965 A | 9/1997 | Bales et al. | |
| 5,667,526 A * | 9/1997 | Levin | 606/207 |
| 5,681,348 A | 10/1997 | Sato | |
| 5,683,359 A | 11/1997 | Farkas et al. | |
| 5,683,385 A | 11/1997 | Kortenbach et al. | |
| 5,683,388 A | 11/1997 | Slater | |
| 5,684,729 A | 11/1997 | Yamada et al. | |
| 5,707,392 A * | 1/1998 | Kortenbach | 606/207 |
| 5,722,421 A * | 3/1998 | Francese et al. | 600/564 |
| 5,741,285 A | 4/1998 | McBrayer et al. | |
| 5,743,906 A | 4/1998 | Parins et al. | |
| 5,746,216 A | 5/1998 | Turturro et al. | |
| 5,746,740 A * | 5/1998 | Nicholas | 606/52 |
| 5,762,613 A | 6/1998 | Sutton et al. | |
| 5,766,199 A | 6/1998 | Heisler et al. | |
| 5,810,876 A * | 9/1998 | Kelleher | 606/205 |
| 5,819,738 A * | 10/1998 | Slater | 600/564 |
| 5,840,043 A | 11/1998 | Palmer et al. | |
| 5,843,000 A | 12/1998 | Nishioka et al. | |
| 5,846,240 A | 12/1998 | Kortenbach et al. | |
| 5,908,437 A | 6/1999 | Asano et al. | |
| 5,919,202 A | 7/1999 | Yoon | |
| 5,924,977 A * | 7/1999 | Yabe et al. | 600/121 |
| 5,951,488 A | 9/1999 | Slater et al. | |
| 5,976,130 A | 11/1999 | McBrayer et al. | |
| 6,010,532 A | 1/2000 | Kroll et al. | |
| 6,024,708 A | 2/2000 | Bales et al. | |
| 6,036,656 A | 3/2000 | Slater | |
| 6,041,679 A | 3/2000 | Slater et al. | |
| RE36,666 E | 4/2000 | Honkanen et al. | |
| 6,074,408 A * | 6/2000 | Freeman | 606/205 |
| RE36,795 E | 7/2000 | Rydell | |
| 6,083,150 A | 7/2000 | Aznoian et al. | |
| 6,099,483 A | 8/2000 | Palmer et al. | |
| 6,129,683 A | 10/2000 | Sutton et al. | |
| 6,139,508 A | 10/2000 | Simpson et al. | |
| 6,149,607 A | 11/2000 | Simpson et al. | |
| 6,159,162 A | 12/2000 | Kostylev et al. | |
| 6,190,399 B1 | 2/2001 | Palmer et al. | |
| 6,193,671 B1 | 2/2001 | Turturro et al. | |
| 6,193,737 B1 | 2/2001 | Ouchi | |
| 6,261,242 B1 | 7/2001 | Roberts et al. | |
| 6,264,617 B1 | 7/2001 | Bales et al. | |
| 6,273,860 B1 * | 8/2001 | Kostylev et al. | 600/564 |
| 6,283,924 B1 | 9/2001 | Ouchi | |
| 6,299,630 B1 | 10/2001 | Yamamoto | |
| 6,309,404 B1 | 10/2001 | Krzyzanowski | |
| 6,368,290 B1 | 4/2002 | Baska | |
| 6,378,351 B1 | 4/2002 | Ouchi et al. | |
| 6,402,728 B2 | 6/2002 | Otsubo | |
| 6,409,678 B1 | 6/2002 | Ouchi | |
| 6,425,910 B1 | 7/2002 | Hugueny et al. | |
| 6,427,509 B1 | 8/2002 | Ouchi et al. | |
| 6,440,085 B1 | 8/2002 | Krzyzanowski | |
| 6,447,511 B1 | 9/2002 | Slater | |
| 6,514,197 B1 | 2/2003 | Ouchi et al. | |
| 6,514,269 B2 | 2/2003 | Yamamoto | |
| 6,551,315 B2 | 4/2003 | Kortenbach et al. | |
| 6,554,850 B1 | 4/2003 | Ouchi et al. | |
| 6,561,988 B1 | 5/2003 | Turturro et al. | |
| 6,569,085 B2 | 5/2003 | Kortenbach et al. | |
| 6,582,451 B1 | 6/2003 | Marucci et al. | |
| 6,613,068 B2 | 9/2003 | Ouchi | |
| 6,616,662 B2 | 9/2003 | Scholer et al. | |
| 6,685,723 B1 | 2/2004 | Ouchi et al. | |
| 6,689,122 B2 | 2/2004 | Yamamoto | |
| 6,692,445 B2 | 2/2004 | Roberts et al. | |

| | | |
|---|---|---|
| 6,716,226 B2 | 4/2004 | Sixto, Jr. et al. |
| 6,740,106 B2 * | 5/2004 | Kobayashi et al. ............ 606/205 |
| 6,743,240 B2 | 6/2004 | Smith et al. |
| 6,767,349 B2 | 7/2004 | Ouchi |
| 6,808,491 B2 | 10/2004 | Kortenbach et al. |
| 6,824,548 B2 | 11/2004 | Smith et al. |
| 6,843,794 B2 | 1/2005 | Sixto, Jr. et al. |
| 6,887,240 B1 * | 5/2005 | Lands et al. ...................... 606/51 |
| 6,926,676 B2 | 8/2005 | Turturro et al. |
| 6,945,979 B2 | 9/2005 | Kortenbach et al. |
| 6,951,560 B1 | 10/2005 | Kidooka |
| 6,953,430 B2 | 10/2005 | Kidooka |
| 6,964,662 B2 | 11/2005 | Kidooka |
| 6,969,389 B2 | 11/2005 | Kidooka |
| 7,033,315 B2 | 4/2006 | Smith |
| 7,037,276 B2 | 5/2006 | Sayet et al. |
| 7,052,489 B2 | 5/2006 | Griego et al. |
| 7,105,000 B2 | 9/2006 | McBrayer |
| RE39,415 E | 11/2006 | Bales et al. |
| 7,147,638 B2 * | 12/2006 | Chapman et al. ................ 606/51 |
| 7,171,839 B2 | 2/2007 | Krzyzanowski |
| 7,186,261 B2 | 3/2007 | Prestel |
| 7,311,674 B2 | 12/2007 | Gingrich et al. |
| 7,326,209 B2 | 2/2008 | Kidooka |
| 7,341,564 B2 | 3/2008 | Zwiefel et al. |
| 7,354,439 B2 | 4/2008 | Kidooka |
| 7,422,592 B2 | 9/2008 | Morley et al. |
| 7,534,253 B2 | 5/2009 | Endara et al. |
| 7,621,910 B2 | 11/2009 | Sugi |
| 7,736,363 B2 | 6/2010 | Watnabe |
| 7,749,222 B2 | 7/2010 | Lu et al. |
| 7,775,989 B2 | 8/2010 | Nakao |
| 2001/0021860 A1 | 9/2001 | Ouchi |
| 2001/0047124 A1 | 11/2001 | Yamamoto |
| 2001/0051812 A1 | 12/2001 | Ouchi |
| 2002/0010459 A1 | 1/2002 | Whittier et al. |
| 2002/0013595 A1 | 1/2002 | Yamamoto |
| 2002/0043973 A1 | 4/2002 | Amini et al. |
| 2002/0068935 A1 | 6/2002 | Kortenbach |
| 2002/0068945 A1 | 6/2002 | Sixto et al. |
| 2002/0068946 A1 | 6/2002 | Kortenbach |
| 2002/0078967 A1 | 6/2002 | Sixto |
| 2002/0138086 A1 | 9/2002 | Sixto |
| 2002/0165580 A1 | 11/2002 | Zwiefel et al. |
| 2002/0173786 A1 | 11/2002 | Kortenbach |
| 2002/0188220 A1 * | 12/2002 | Krzyzanowski .............. 600/567 |
| 2002/0198537 A1 | 12/2002 | Smith |
| 2002/0198538 A1 | 12/2002 | Kortenbach |
| 2002/0198539 A1 | 12/2002 | Sixto |
| 2002/0198540 A1 | 12/2002 | Smith |
| 2002/0198541 A1 | 12/2002 | Smith et al. |
| 2002/0198549 A1 | 12/2002 | Sixto et al. |
| 2003/0009193 A1 | 1/2003 | Corsaro |
| 2003/0036679 A1 | 2/2003 | Kortenbach et al. |
| 2003/0050574 A1 | 3/2003 | Krueger |
| 2003/0097147 A1 | 5/2003 | Prestel |
| 2003/0144605 A1 | 7/2003 | Burbank |
| 2003/0191464 A1 | 10/2003 | Kidooka |
| 2003/0191478 A1 | 10/2003 | Kortenbach et al. |
| 2003/0195387 A1 | 10/2003 | Kortenbach et al. |
| 2003/0233092 A1 | 12/2003 | Kortenbach et al. |
| 2003/0236549 A1 | 12/2003 | Bonadio et al. |
| 2004/0015165 A1 | 1/2004 | Kidooka |
| 2004/0068291 A1 | 4/2004 | Suzuki |
| 2004/0079831 A1 * | 4/2004 | McNeil et al. ............ 242/420.6 |
| 2004/0087979 A1 | 5/2004 | Field et al. |
| 2004/0092967 A1 | 5/2004 | Sancoff et al. |
| 2004/0093019 A1 | 5/2004 | Kothe |
| 2004/0097831 A1 * | 5/2004 | Bourne et al. ................ 600/564 |
| 2004/0098040 A1 | 5/2004 | Taniguchi et al. |
| 2004/0116948 A1 | 6/2004 | Sixto et al. |
| 2004/0193186 A1 | 9/2004 | Kortenbach et al. |
| 2004/0193214 A1 | 9/2004 | Scheller et al. |
| 2004/0199160 A1 | 10/2004 | Slater |
| 2004/0249411 A1 | 12/2004 | Suzuki |
| 2004/0254592 A1 | 12/2004 | DiCarlo et al. |
| 2004/0260198 A1 | 12/2004 | Rothberg et al. |
| 2004/0260337 A1 | 12/2004 | Freed |
| 2005/0004432 A1 | 1/2005 | Suzuki et al. |
| 2005/0033333 A1 | 2/2005 | Smith et al. |
| 2005/0033354 A1 | 2/2005 | Montalvo et al. |
| 2005/0043758 A1 | 2/2005 | Golden et al. |
| 2005/0049520 A1 * | 3/2005 | Nakao ........................... 600/562 |
| 2005/0049616 A1 | 3/2005 | Rivera |
| 2005/0049633 A1 | 3/2005 | Watanabe |
| 2005/0054945 A1 | 3/2005 | Cohen et al. |
| 2005/0090837 A1 | 4/2005 | Sixto et al. |
| 2005/0090838 A1 | 4/2005 | Sixto et al. |
| 2005/0113867 A1 | 5/2005 | Anderhub et al. |
| 2005/0124912 A1 | 6/2005 | Griego et al. |
| 2005/0125010 A1 | 6/2005 | Smith et al. |
| 2005/0131312 A1 | 6/2005 | Endara et al. |
| 2005/0137585 A1 | 6/2005 | Landman et al. |
| 2005/0216029 A1 | 9/2005 | Gingrich et al. |
| 2005/0240218 A1 | 10/2005 | Freed et al. |
| 2005/0261735 A1 | 11/2005 | Shibata |
| 2006/0009711 A1 | 1/2006 | Gingrich et al. |
| 2006/0025780 A1 | 2/2006 | James |
| 2006/0149222 A1 | 7/2006 | Okada |
| 2006/0184198 A1 | 8/2006 | Bales et al. |
| 2006/0206145 A1 | 9/2006 | Griego et al. |
| 2006/0276785 A1 * | 12/2006 | Asahara et al. ................. 606/51 |
| 2007/0055172 A1 | 3/2007 | Ratnakar |
| 2007/0078458 A1 | 4/2007 | Dumbauld et al. |
| 2007/0149971 A1 | 6/2007 | Nishimura |
| 2007/0198011 A1 | 8/2007 | Sugita |
| 2007/0244507 A1 | 10/2007 | Szweda et al. |
| 2007/0244508 A1 | 10/2007 | Weizman et al. |
| 2007/0244509 A1 | 10/2007 | Weizman et al. |
| 2007/0244510 A1 | 10/2007 | Weizman et al. |
| 2007/0244511 A1 | 10/2007 | Weizman et al. |
| 2007/0244512 A1 | 10/2007 | Measamer |
| 2007/0244513 A1 | 10/2007 | Weizman et al. |
| 2007/0244514 A1 | 10/2007 | Weizman et al. |
| 2008/0064982 A1 | 3/2008 | Nowlin et al. |
| 2008/0125769 A1 | 5/2008 | Suzuki et al. |
| 2008/0171908 A1 | 7/2008 | Okada et al. |
| 2008/0194910 A1 | 8/2008 | Miyamoto et al. |
| 2009/0088738 A1 | 4/2009 | Guerra et al. |
| 2009/0088739 A1 | 4/2009 | Hushka et al. |
| 2009/0088740 A1 | 4/2009 | Guerra et al. |
| 2009/0088741 A1 | 4/2009 | Hushka et al. |
| 2009/0088744 A1 | 4/2009 | Townsend |
| 2009/0088745 A1 | 4/2009 | Hushka et al. |
| 2009/0088746 A1 | 4/2009 | Hushka et al. |
| 2009/0088747 A1 | 4/2009 | Hushka et al. |
| 2009/0131933 A1 | 5/2009 | Ghabrial et al. |
| 2009/1013193 | 5/2009 | Vakharia et al. |
| 2009/0216078 A1 | 8/2009 | Iwanaga et al. |
| 2009/0264918 A1 | 10/2009 | Endara et al. |
| 2009/0287112 A1 | 11/2009 | Freeman |
| 2010/0106068 A1 | 4/2010 | Karpiel et al. |

FOREIGN PATENT DOCUMENTS

| | | |
|---|---|---|
| DE | 85 32 644.5 U1 | 5/1986 |
| DE | 87 12 328.2 U1 | 3/1988 |
| DE | 88 14 560.3 U1 | 3/1989 |
| DE | 39 20 706 A1 | 1/1991 |
| DE | 40 06 673 A1 | 9/1991 |
| DE | 40 12 882 C2 | 3/1992 |
| DE | 92 11 834.8 U1 | 4/1993 |
| DE | 296 14 931 U1 | 3/1997 |
| DE | 199 04 723 A1 | 8/1999 |
| DE | 199 48 387 A1 | 5/2000 |
| DE | 100 18 674 A1 | 11/2000 |
| DE | 100 48 369 A1 | 4/2001 |
| DE | 100 51 651 A1 | 4/2001 |
| DE | 100 56 946 A1 | 5/2001 |
| DE | 100 43 163 A1 | 6/2001 |
| DE | 101 10 929 A1 | 9/2001 |
| DE | 101 28 553 A1 | 1/2002 |
| DE | 101 23 848 A1 | 3/2002 |
| DE | 101 56 313 A1 | 6/2003 |
| DE | 103 16 134 A1 | 10/2003 |
| DE | 100 48 369 C2 | 12/2003 |
| DE | 103 32 613 A1 | 2/2004 |
| DE | 10 2004 031 703 A1 | 3/2005 |
| DE | 600 09 733 T2 | 3/2005 |

| | | | | | | |
|---|---|---|---|---|---|---|
| DE | 100 18 674 B4 | 6/2005 | | JP | 2001-029349 A | 2/2001 |
| DE | 103 53 006 A1 | 6/2005 | | JP | 2001-070239 | 3/2001 |
| DE | 697 31 096 T2 | 10/2005 | | JP | 2001-070239 A | 3/2001 |
| DE | 10 2005 023 852 A1 | 12/2005 | | JP | 2001-070308 A | 3/2001 |
| DE | 100 51 652 B4 | 2/2006 | | JP | 2001-070309 A | 3/2001 |
| DE | 103 53 006 B4 | 2/2006 | | JP | 2001-079009 | 3/2001 |
| EP | 0 207 829 A1 | 1/1987 | | JP | 2001-095807 | 4/2001 |
| EP | 0 207 830 A1 | 1/1987 | | JP | 2001-095807 A | 4/2001 |
| EP | 317 526 | 5/1989 | | JP | 2001-095808 A | 4/2001 |
| EP | 0 380 874 A1 | 8/1990 | | JP | 2001-104318 A | 4/2001 |
| EP | 0 507 620 B1 | 10/1992 | | JP | 2001-112763 A | 4/2001 |
| EP | 0 593 929 A1 | 9/1993 | | JP | 2001-112764 A | 4/2001 |
| EP | 0 573 817 A1 | 12/1993 | | JP | 2001-112765 A | 4/2001 |
| EP | 0 367 818 B1 | 3/1994 | | JP | 2001-137998 A | 5/2001 |
| EP | 0 585 921 A1 | 3/1994 | | JP | 3190029 B2 | 5/2001 |
| EP | 0 598 607 A2 | 5/1994 | | JP | 2001-190556 A | 7/2001 |
| EP | 0 491 890 B1 | 2/1996 | | JP | 3220164 B2 | 8/2001 |
| EP | 0 592 243 B1 | 4/1997 | | JP | 3220165 B2 | 8/2001 |
| EP | 0 621 009 B1 | 7/1997 | | JP | 2001-245891 A | 9/2001 |
| EP | 0 573 817 B1 | 7/1998 | | JP | 2001-321385 A | 11/2001 |
| EP | 1 312 313 A1 | 5/2003 | | JP | 2001-321386 A | 11/2001 |
| EP | 1 371 332 A1 | 12/2003 | | JP | 2001-340347 A | 12/2001 |
| EP | 1 001 706 B1 | 3/2004 | | JP | 2002-017734 A | 1/2002 |
| EP | 1 221 896 B1 | 4/2004 | | JP | 2002-034989 A | 2/2002 |
| EP | 1 462 063 A1 | 9/2004 | | JP | 2002-045363 A | 2/2002 |
| EP | 0 921 758 B1 | 10/2004 | | JP | 2002-065598 A | 3/2002 |
| EP | 1 472 982 A2 | 11/2004 | | JP | 2002-119514 A | 4/2002 |
| EP | 1 161 183 B1 | 10/2005 | | JP | 2003-093393 A | 4/2002 |
| EP | 1 607 049 A1 | 12/2005 | | JP | 2002-153475 A | 5/2002 |
| EP | 1 607 050 A1 | 12/2005 | | JP | 2002-191605 A | 7/2002 |
| EP | 1 607 055 A1 | 12/2005 | | JP | 2002-191606 A | 7/2002 |
| EP | 1 872 730 | 1/2008 | | JP | 2002-282265 A | 10/2002 |
| EP | 1 875 872 | 1/2008 | | JP | 2002-330973 A | 11/2002 |
| FR | 2 751 199 A1 | 1/1998 | | JP | 2003-126103 A | 5/2003 |
| FR | 2 864 888 A1 | 7/2005 | | JP | 2003-235851 A | 8/2003 |
| JP | 2-1251 | 1/1990 | | JP | 2003-299669 | 10/2003 |
| JP | 06-217987 A | 8/1993 | | JP | 2003-310635 | 11/2003 |
| JP | 05-309097 A | 11/1993 | | JP | 2004-000424 A | 1/2004 |
| JP | 06-189966 A | 7/1994 | | JP | 2004-049330 A | 2/2004 |
| JP | 06-197906 A | 7/1994 | | JP | 2004-97615 | 4/2004 |
| JP | 07-313514 A | 12/1995 | | JP | 3569469 B2 | 6/2004 |
| JP | 08-206120 A | 8/1996 | | JP | 2004-229976 | 8/2004 |
| JP | 09-075356 A | 3/1997 | | JP | 2005-021346 A | 1/2005 |
| JP | 09-098978 A | 4/1997 | | JP | 2005-058344 | 3/2005 |
| JP | 09-507150 | 7/1997 | | JP | 2005-152463 A | 6/2005 |
| JP | 09-508561 T2 | 9/1997 | | JP | 2005-193061 | 7/2005 |
| JP | 09-276285 | 10/1997 | | JP | 2005-224426 A | 8/2005 |
| JP | 10-024045 | 1/1998 | | JP | 2005-237431 | 9/2005 |
| JP | 10-024045 A | 1/1998 | | JP | 2006-296578 | 11/2006 |
| JP | 10-028692 A | 2/1998 | | JP | 2006-296781 | 11/2006 |
| JP | 10-118015 A | 5/1998 | | JP | 2006-334267 | 12/2006 |
| JP | 10-118076 A | 5/1998 | | JP | 2006-334348 | 12/2006 |
| JP | 10-118091 A | 5/1998 | | JP | 2007-260248 | 10/2007 |
| JP | 10-137251 A | 5/1998 | | JP | 2007-330436 | 12/2007 |
| JP | 10-165408 A | 6/1998 | | JP | 2009-153535 | 7/2009 |
| JP | 10-506035 | 6/1998 | | JP | 2009-297503 | 12/2009 |
| JP | 09-276285 A | 10/1998 | | WO | WO 89/10093 A1 | 11/1989 |
| JP | 11-019085 A | 1/1999 | | WO | WO 90/01297 A1 | 2/1990 |
| JP | 11-19086 | 1/1999 | | WO | WO 91/16856 A1 | 11/1991 |
| JP | 11-19087 | 1/1999 | | WO | WO 93/20754 | 10/1993 |
| JP | 11-033032 A | 2/1999 | | WO | WO 94/17741 | 8/1994 |
| JP | 11-047135 A | 2/1999 | | WO | WO 96/09004 | 3/1996 |
| JP | 11-076244 A | 3/1999 | | WO | WO 96/09004 A1 | 3/1996 |
| JP | 11-155877 | 6/1999 | | WO | WO 96/19144 A1 | 6/1996 |
| JP | 11-178829 | 7/1999 | | WO | WO 97/11643 | 4/1997 |
| JP | 11-509132 T2 | 8/1999 | | WO | WO 97/12558 A1 | 4/1997 |
| JP | 11-509459 T2 | 8/1999 | | WO | WO 97/01776 A1 | 11/1997 |
| JP | 2000-175920 A | 6/2000 | | WO | WO 97/41777 A1 | 11/1997 |
| JP | 2000-175928 A | 6/2000 | | WO | WO 98/03116 A1 | 1/1998 |
| JP | 2000-189429 A | 7/2000 | | WO | WO 98/06336 A1 | 2/1998 |
| JP | 2000-189430 A | 7/2000 | | WO | WO 98/26723 A1 | 6/1998 |
| JP | 2000-189431 | 7/2000 | | WO | WO 99/07287 A1 | 2/1999 |
| JP | 2000-189432 A | 7/2000 | | WO | WO 00/01304 A1 | 1/2000 |
| JP | 2000-189433 A | 7/2000 | | WO | WO 00/07502 A1 | 2/2000 |
| JP | 2000-189434 A | 7/2000 | | WO | WO 00/54658 A1 | 9/2000 |
| JP | 2000-189435 A | 7/2000 | | WO | WO 01/24706 A1 | 4/2001 |
| JP | 2000-271128 | 10/2000 | | WO | WO 01/28427 A1 | 4/2001 |
| JP | 2000-296131 A | 10/2000 | | WO | WO 03/000115 A2 | 1/2003 |
| JP | 3150157 B2 | 1/2001 | | WO | WO 03/024300 A1 | 3/2003 |

| | | | | | | |
|---|---|---|---|---|---|---|
| WO | WO 03/028557 A1 | 4/2003 | | WO | WO 2005/072663 A1 | 8/2005 |
| WO | WO 03/099139 A1 | 12/2003 | | WO | WO 2006/114952 | 11/2006 |
| WO | WO 2005/009255 A1 | 2/2005 | | WO | WO 2006/114989 | 11/2006 |
| WO | WO 2005/025432 A1 | 3/2005 | | | | |
| WO | WO 2005/041789 A1 | 5/2005 | | | | |
| WO | WO 2005/063127 A1 | 7/2005 | | * cited by examiner | | |

ENDOSCOPIC INSTRUMENTS

CROSS-REFERENCE TO RELATED APPLICATION

This application claims the benefit under 35 U.S.C. §§119, 120 of U.S. Provisional Application No. 60/479,145 to Elliott ROTHBERG and William GIL DE MONTES entitled BIOPSY FORCEPS CUTTER WITH RADIUSED FEATURES and filed on Jun. 18, 2003.

DESCRIPTION OF THE INVENTION

1. Field of the Invention

Embodiments of the invention include a medical device with one or more of a variety of features. More particularly, embodiments of the invention relate to endoscopic devices that include one or more features that improve the use of the device. Examples of such features include chamfered edges and corners on, for example, the end effectors, a surface with a controlled finish also on, for example, the end effectors, a jaw with teeth and/or a tang having various configurations, a handle having soft-grip features, and/or an elongate member with varied rigidity.

2. Background of the Invention

Various medical instruments may be used in connection with an endoscope for performing a number of operations at a site deep within a patient's body cavity. One such instrument, a biopsy forceps device, samples tissue from a body cavity with minimal intervention and discomfort to patients. Typically, a biopsy forceps device, like other endoscopic instruments, has a long flexible tubular member for insertion into a lumen of an endoscope. The tubular member is sufficiently long and flexible to follow a long, winding path of the body cavity. An end effector assembly, such as a biopsy forceps assembly, is attached at a distal end of the tubular member, and a handle is attached at a proximal end of the tubular member. The handle may have an elongate portion and a spool portion disposed around the elongate portion. The spool portion may be configured to move longitudinally relative to the elongate portion. An elongate mechanism, such as one or more pull wires, extends through the tubular member to connect the end effector assembly and a portion of the handle, such as the spool portion. Longitudinal movement of the spool portion relative to the elongate portion of the handle causes the elongate mechanism to move longitudinally in the tubular member, which in turn causes the actuation of the end effector assembly.

In methods of using the biopsy forceps device, an endoscope is placed in a patient's body cavity adjacent a tissue site from which the acquisition of a tissue sample is desired. The biopsy forceps device is then advanced to the tissue site via a working channel of the endoscope. Once the biopsy forceps device is next to the portion of the tissue from which the acquisition of a tissue sample is desired, the spool portion is moved relative to the elongate portion so as to move pull wires. The movement of the pull wires causes the jaws of the biopsy forceps assembly to open.

The open jaws are then advanced to the tissue site, and the spool portion is again moved relative to the elongate portion so as to move the pull wires such that the jaws close. The closing of the jaws causes a tissue sample to be captured in the end effector assembly. The biopsy forceps device is then removed from the body cavity via the working channel of the endoscope.

SUMMARY OF THE INVENTION

In accordance with the invention, an embodiment of the invention includes a medical device including a handle, an end effector assembly, and a member connecting the handle to the end effector assembly. The end effector assembly includes an end effector having non-sharp edges and corners.

Another embodiment of the invention includes a medical device including a handle, an end effector assembly, and a member connecting the handle to the end effector assembly. Portions of the end effector assembly have a roughened surface.

Yet another embodiment of the invention includes a medical device including a handle, an end effector assembly, and a member connecting the handle to the end effector assembly. The end effector assembly includes opposing jaw portions each including a plurality of teeth. Each of the teeth includes a crest, a root, and an intermediate portion between the crest and the root. The intermediate portions of opposing jaw portions are configured to contact each other when the opposing jaw portions are brought together and the root has a recessed portion configured to accommodate a sharp, pointed tip of the crest.

Still another embodiment of the invention includes a medical device including a handle, an end effector assembly, and a member connecting the handle to the end effector assembly. The end effector assembly includes at least one end effector having a tang defining a mounting hole configured to receive one of a wire and an axle and the tang includes a portion disposed around the mounting hole that has a thickness greater than a thickness of other portions of the tang.

A further embodiment of the invention includes a medical device including a handle, an end effector assembly, and a member connecting the handle to the end effector assembly. The end effector assembly includes at least one biopsy jaw having a tissue receiving portion that defines at least one hole configured so as to substantially prevent contact between an edge of the hole and a tube-like member in which the end effector assembly is configured to extend through.

A yet further embodiment of the invention includes a medical device including a soft-grip handle, an end effector assembly, and a member connecting the handle to the end effector assembly.

A still further embodiment of the invention includes a medical device including a handle, an end effector assembly, and an elongate, flexible member connecting the handle to the end effector assembly. A proximal portion of a distal third of the elongate member is more flexible than adjacent portions of the elongate member.

Another embodiment of the invention includes a medical device including a handle, an end effector assembly, and an elongate, flexible member connecting the handle to the end effector assembly. The end effector assembly includes a pair of opposing biopsy jaws each having a tissue receiving portion having a roughened surface and defining a hole, the hole configured so as to substantially prevent contact between an edge of the hole and a tube-like member in which the end effector assembly is configured to extend through. Each biopsy jaw further includes a tang defining a mounting hole configured to receive one of a wire and an axle, the tang including a portion disposed around the mounting hole that has a thickness greater than a thickness of other portions of the tang. Each biopsy jaw further includes a plurality of teeth, each of the teeth including a crest, a root, and an intermediate portion between the crest and the root. The intermediate portions of opposing biopsy jaws are configured to contact each other when the biopsy jaws are brought together, and the root has a recessed portion configured to accommodate a sharp, pointed tip of the crest.

Various embodiments of the invention may have any or all of the following features. wherein the end effector defines a hole having a non-sharp edge. The end effector may include a jaw extending from an arm, and wherein all edges of the jaw other than a cutting edge of the jaw are non-sharp. The non-sharp edges and corners may be beveled. Portions of the end effector assembly may have a rougher surface than other portions of the end effector assembly. The end effector assembly may include a biopsy forceps jaw having a roughened surface. The roughened surface of the biopsy forceps jaws may be an outer surface of the biopsy forceps jaw. The roughened surface of the biopsy forceps jaws may be an inner surface of the biopsy forceps jaw. The roughened surface may be formed by one of grit blasting, media tumbling, plating, sputtering, photo-etching, acid-etching, and plasma coating. The root may be at least a partial, substantially circular cutout. A center of the cutout may be displaced vertically relative to adjacent intermediate portions. A center of the cutout may be displaced horizontally relative to a center of adjacent intermediate portions. The root may be a U-shaped groove. A center of the U-shaped groove may be displaced vertically relative to adjacent intermediate portions. A center of the U-shaped groove may be displaced horizontally relative to a center of adjacent intermediate portions. A gap may be between the tip and the root of opposing teeth when the opposing jaw portions are brought together. A wire having a first wire portion may be substantially contacting one side of the tang and a second wire portion substantially contacting another side of the tang. The at least one end effector may include two end effectors. The wire may be bent on both sides of the mounting hole. A section of the tang defining a through hole may be folded so that the through hole is substantially aligned with the mounting hole. The at least one end effector may define a second mounting hole configured to receive the other of the wire and the axle, and wherein the tang includes a second portion around the second mounting hole that has a thickness greater than the thickness of other portions of the tang. The hole may be disposed off a centerline of the biopsy jaw. The at least one biopsy jaw may include two biopsy jaws. The at least one hole may include a plurality of holes. The handle may have a ring portion connected to an elongate portion, and a spool portion disposed around the elongate portion, and wherein the ring portion and the spool portion have a soft-grip configuration. The handle may have a plurality of finger rings, and wherein the finger rings have a soft-grip configuration. The soft-grip handle may include a low durometer material. The soft-grip handle may include at least one of santoprene and urethane.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

The foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate embodiments of the invention and together with the description, serve to explain the principles of the invention.

DESCRIPTION OF THE EMBODIMENTS

Reference will now be made in detail to the present exemplary embodiments of the invention illustrated in the accompanying drawings. Wherever possible, the same reference numbers will be used throughout the drawings to refer to the same or like parts.

Figure 1:
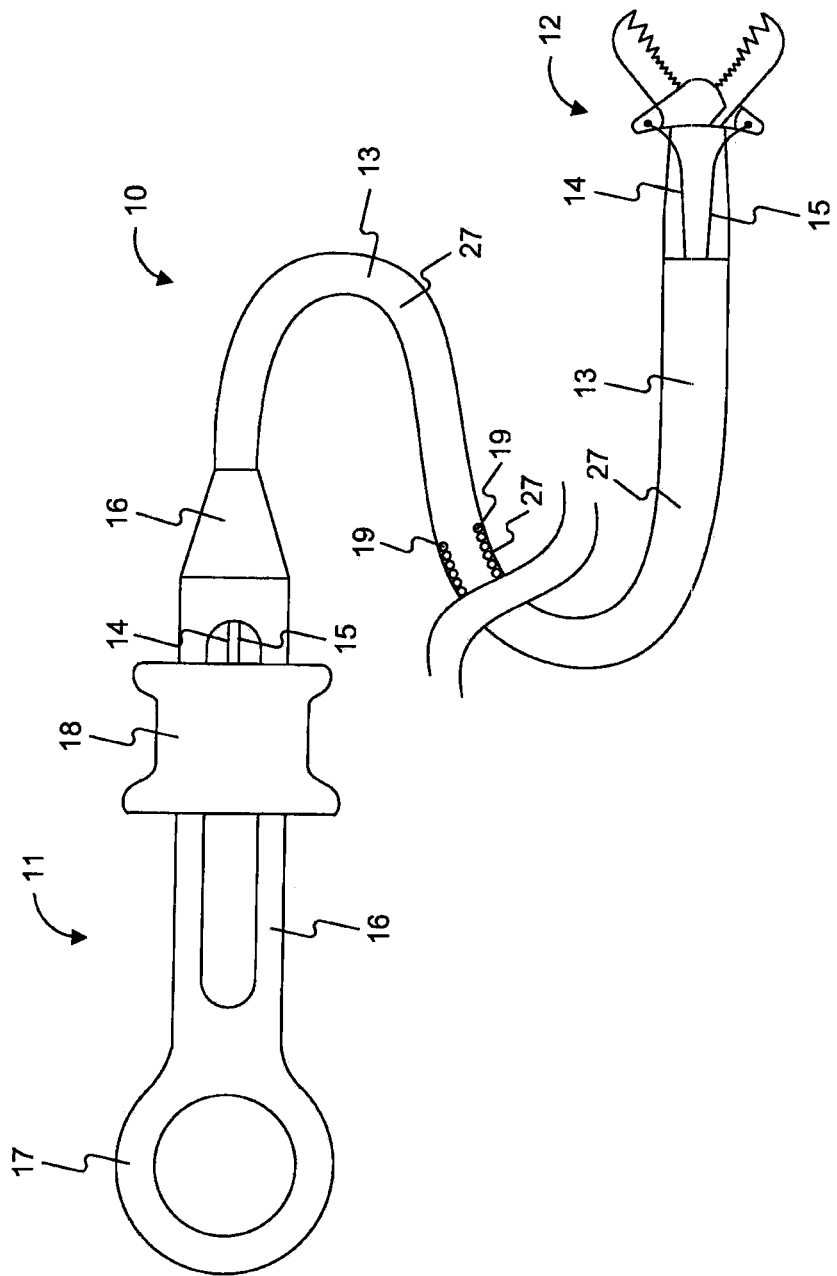
FIG. 1 is a perspective view of an endoscopic instrument suitable for use in connection with embodiments of the present invention.

An exemplary embodiment of a medical device is depicted in FIG. 1. The medical device is an endoscopic instrument 10 that includes a handle portion 11 and an end effector assembly 12 connected to each other by a flexible elongate member 13. Control wires 14, 15 extend between the handle portion 11 and the end effector assembly 12 via a lumen in the flexible elongate member 13. The handle portion 11 includes an elongate portion 16 connected at its proximal end to a ring portion 17 and a spool portion 18 slidably disposed around the elongate portion 16. The elongate member 13 may having a coiled portion 19 (partially shown in FIG. 1) covered by an outer jacket or a sheath 27. However, the elongate member 13 may not have a coiled portion 19, and instead may include a single layer tubular member. The end effector assembly 12 may be any type of assembly, for example, a biopsy forceps jaw as depicted in FIG. 1. The control wires 14, 15 may be connected at their distal ends to opposing portions of the end effector assembly 12, and at their proximal ends to spool portion 18. Longitudinal movement of the spool portion 18 relative to the elongate portion 16 causes the actuation of the end effector assembly 12 via the control wires 14, 15. Portions of the control wires 14, 15 disposed in the handle 16 may be contained within a tube also disposed in the handle 16. The tube may provide the compressive strength that may be needed to actuate the end effector assembly 12.

Figure 2:
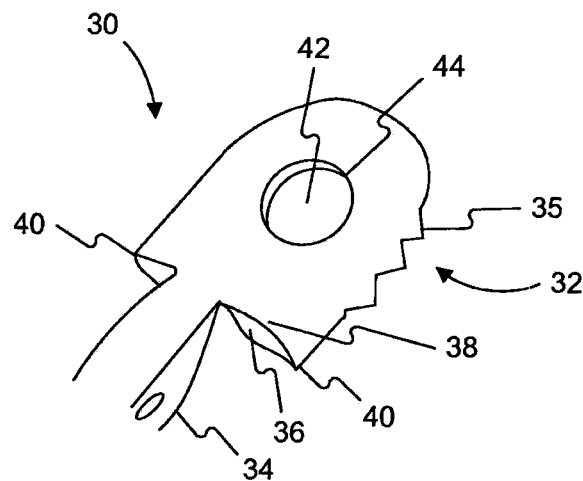
FIG. 2 is a perspective view of a jaw portion of an endoscopic instrument.

A current biopsy forceps jaw 30, such as that shown in FIG. 2, includes a jaw 32 extending from an arm 34. Jaw 32 includes a sharp edge or teeth 35 at its cutting edge. Teeth 35 may mate with another biopsy forceps jaw, of like or similar construction, of an endoscopic forceps instrument to obtain a biopsy sample. Jaw 32 also includes flat surfaces on various parts of jaw 32. For example, the back or proximal-most surface 36 of jaw 32 and certain surfaces intersecting with surface 36 may be flat. The intersection of those surfaces will result in sharp corners and edges, such as edges 38 and corners 40. Jaw 32 also defines a fenestration hole 42 that may include a sharp edge 44. Many current biopsy forceps jaws have such a construction because they are cast from a molded plastic pattern. Certain efficiencies in the manufacture of injection molds lead to flat, intersecting planes and sharp edges and corners of the resultant jaws. These sharp edges and corners, however, may get caught within an endoscope working channel upon entry or exit of a biopsy forceps device through that channel or at the distal end of the endoscope upon re-entry of the forceps after use.

Figure 3:
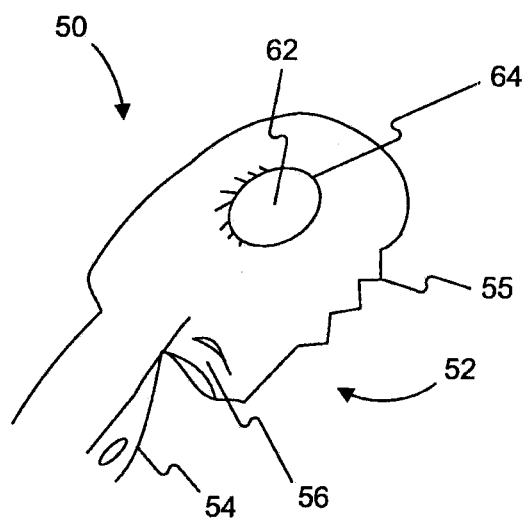
FIG. 3 is a perspective view of a jaw portion of an endoscopic instrument according to an embodiment of the present invention.

Embodiments of the invention include a medical device or portions of the medical device with chamfered corners and/or edges. FIG. 3 shows a biopsy forceps jaw 50 according to an exemplary embodiment of the present invention. The biopsy forceps jaw 50 includes a jaw 52 extending from an arm 54. Like jaw 32 of FIG. 2, jaw 52 includes a sharp edge or teeth 55 at a cutting edge. Unlike jaw 32, however, certain surfaces of jaw 52 are not substantially flat and, instead, are rounded at least near the edges of those surfaces. The corners and edges of various intersecting surfaces are therefore chamfered, beveled, rounded, and/or radiused off and not sharp. For example, the back or proximal-most surface 56 of jaw 52 and certain surfaces intersecting with surface 56 are rounded at least near the edges of those surfaces so that there are no, or fewer, sharp edges or corners associated with jaw 32 (other than the sharp cutting edge having teeth). Jaw 52 also defines a fenestration hole 62 that may include an edge 64 that is rounded, chamfered, beveled, and/or radiused, off so that there is not a sharp edge. The resulting jaw will have no, or fewer, sharp edges or corners to catch within an endoscope working channel upon entry or exit of a biopsy forceps device through that channel or at the distal end of the endoscope upon re-entry of the forceps after use. Less interference with at least the distal section of the endoscope results.

Providing a medical device, or portions thereof, with non-sharp edges and corners may apply to other types of end effectors or other parts of endoscopic or non-endoscopic instruments, including, but not limited to graspers, scissors, forceps, or other laproscopic, endoscopic, or other devices. For example,. the medical device may have a sharp cutting edge that is a radial edge (i.e., a straight cutting edge with no teeth). Other edges, corners, and surface intersections, aside from those mentioned above, may be rounded, chamfered, beveled, and/or radiused off as desired to minimize the effects associated with sharp regions as the device is being used. For example, other portions of the end effector assembly, including tang portions, clevis portions, and/or axle portions may include rounded, chamfered, beveled, and/or radiused off edges and corners.

Figure 5:
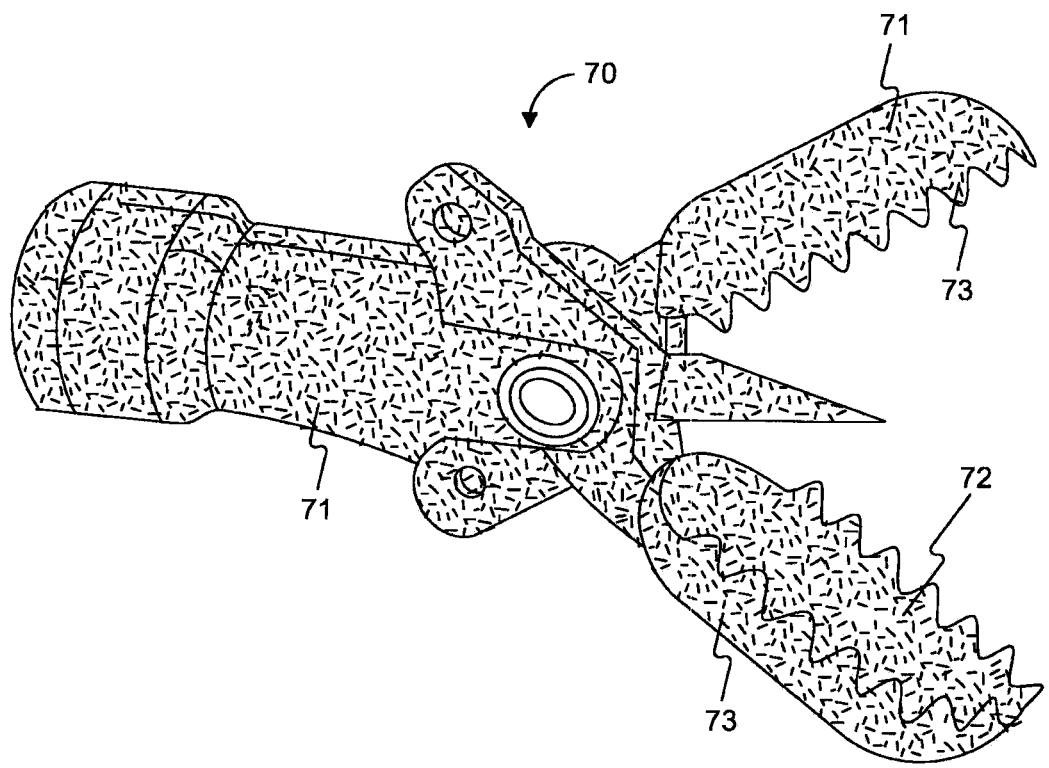
FIG. 5 is a perspective view of a jaw assembly of an endoscopic instrument according to an embodiment of the present invention.

Embodiments of the invention include a medical device or portions of the medical device having a controlled surface finish, including a roughened surface finish. FIG. 5 shows the inner surface 72 and outer surface 71 of a biopsy forceps jaw assembly 70 having a rough surface finish. While FIG. 5 shows a biopsy forceps jaw assembly 70 having all parts with a roughened surface, less than all of the parts of the jaw assembly 70 may include a roughened or textured surface. For example, to attain many of the advantaged described herein, it may be desirable for only the jaws 73, or portions of the jaws 73 such as the outer surface 71, to have a roughened or otherwise textured surface.

Tissues are less prone to sticking to surfaces of jaws having a rough finish than surfaces of jaws having a smooth finish. For example, tissue samples cut with the roughened jaws 73 may be less prone to sticking to the surfaces 71, 72 of the jaws 73. By lessening the smoothness of the inner surface 72 of the jaws 73, the tissue sample may be more easily removed from the jaws 73, for example, when the tissue sample is discharged into an external container.

One potential advantage of having a controlled roughness on the surface of the jaws is that by reducing the amount of sticking, surface contact, and/or seal between the tissue samples and the biopsy jaws, the amount of time spent in a biopsy tissue acquisition procedure is reduced. For example, the amount of time spent trying to release the surface contact between the tissue samples and the surfaces of the jaws, during multiple sample acquisition and/or removing the samples from the jaws into an external specimen container, is reduced. This may permit faster turnaround when a single bite biopsy forceps assembly needs to be removed from an endoscope, the tissue sample retrieved from the jaw, and the assembly reinserted into the endoscope to obtain a subsequent sample.

Another potential advantage for having a rough finish on the surface of the endoscopic instrument is that it reduces surface contact between jaws and/or prevents surfaces of the jaws from sealing and/or sticking to each other. Smooth surfaces may sometimes stick together and form a seal, particularly if a fluid is placed between the surfaces. Having a rough finish on the surface of the jaws reduces the force with which that particular surface of the jaws will stick to either each other or another surface. For example, the surfaces of the teeth of opposing jaws may be less prone to sticking to each other when brought together.

Yet another potential advantage for controlling the surface finish of an endoscopic instrument is that it may provide a more consistent feel and/or performance to the user. For example, the entire endoscopic instrument may have a particular finish, or portions of the endoscopic instrument, such as the end effectors, may have different finishes.

A further potential advantage for controlling the surface finish of an endoscopic instrument is that, for example, when an optimum level of roughness is provided to the surface of the jaw assembly, tissue is more readily grasped and retained in the jaws, for example, so that multiple samples may be collected with a single bite forceps. The controlled surface texture may allow a user to obtain subsequent tissue samples with the prior sample(s) remaining within the jaws. A particular texture of the jaws may allow the tissue sample to be retained within the open jaws while the user acquires a second sample.

A still further potential advantage for controlling the surface finish of an endoscopic instrument is that, for example, when an optimum level of roughness is provided to the surface of the jaw assembly, the roughened surface may assist in both retaining and removing the sample. Such assistance may be dependent on the presence or absence of an external force. For example, when there is no external force exerted on the sample, the roughened surface may assist in the retention of the sample. In another example, when an external force is applied to the sample, the roughened surface may assist in the removal of the sample.

The roughness of the surfaces 71, 72 of the jaw assembly 70 may be created and/or adjusted, for example, by controlling the casting of the jaws 73 and/or subsequent processing of the jaw assembly 70. Subsequent processing may including grit blasting, media tumbling, and/or any other suitable surface finishing technique. The surfaces 71, 72 of the jaw assembly 70 could also be plated, sputtered, photo-etched, acid-etched, and/or plasma coated to control the roughness of the surface. The surface or surfaces of the endoscopic instrument may have a roughness in the range of a few hundred microinches, and may be varied, for example, by increments of a few hundred microinches. The relative roughness of the surface or surfaces of the endoscopic instrument may be varied with respect to each other. For example, one surface or portion of a surface may have a relatively rough finish, while another surface or portion of a surface may have a relatively smooth finish.

Providing surface(s) of a medical device, or portions thereof, with a controlled finish, for example a roughened surface, may apply to other types of end effectors or other parts of endoscopic or non-endoscopic instruments, including, but not limited to graspers, scissors, forceps, or other laproscopic, endoscopic, or other devices. Furthermore, other portions of the end effector assembly, including tang portions, clevis portions, and/or axle portions may include surfaces with a controlled finish, for example, a roughened surface. Additionally, only specific portions of parts of the end effector assembly may have a controlled finish. For example, only the inner surfaces of a the jaws of an end effector assembly may have a roughened surface.

Figure 8A:
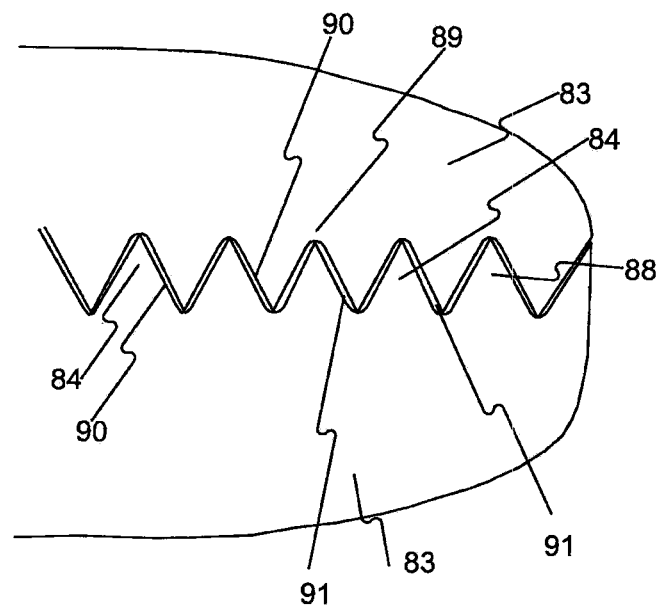
FIG. 8A is a side view of mated jaw portions of an endoscopic instrument.
Figure 8B:
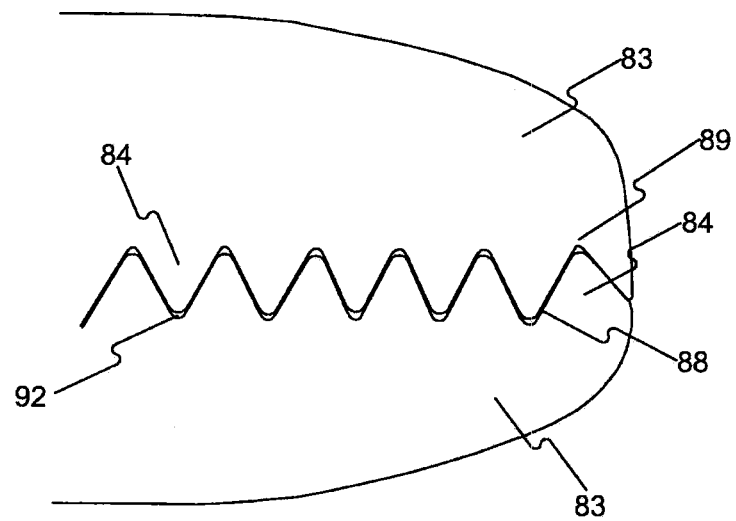
FIG. 8B is a side view of mated jaw portions of an endoscopic instrument.

Views of mated jaw portions 83 of endoscopic instruments are shown in FIGS. 8A and 8B. Each jaw portion 83 has teeth 84, with each tooth 84 having a crest portion 88. A root portion 89 is disposed between each set of adjoining teeth 84. Substantially diagonal portions 90 of the teeth 84 are disposed between the crest 88 and the root 89 to form the tooth.

The configuration of the root 89 may limit the configuration of the teeth. For example, in order for opposing teeth 84 to fit together, the substantially diagonal portions 90 of teeth 84 on opposing jaw portions 83 need to meet before the crest 88 contacts the root 89. Otherwise, a gap 91 will form between the substantially diagonal portions 90 of opposing jaw portions 83, as shown in FIG. 8A. The gap 91 may prevent the opposing jaw portions 83 and teeth 84 from performing an effective cutting action. Though FIG. 8A includes jaws 83 having teeth 84 with sharp tips to enhance biting action, it may be difficult to fabricate jaws (such as through stamping) that have matching sharp-cornered roots 89.

In some cases, to ensure the opposing jaws portions 83 fully close, as shown in FIG. 8B, the crest portion 88 may be given a radius (about 0.005 inches) slightly larger than the radius of the root portion 89 (such as about 0.003 inches). A gap 92 is formed between the crest portion 88 of one jaw portion 83 and the root portion 89 of an opposing jaw portion 83. However, this jaw configuration includes teeth with non-sharp tips (i.e. crests) inhibiting optimal cutting performance.

Figure 6:
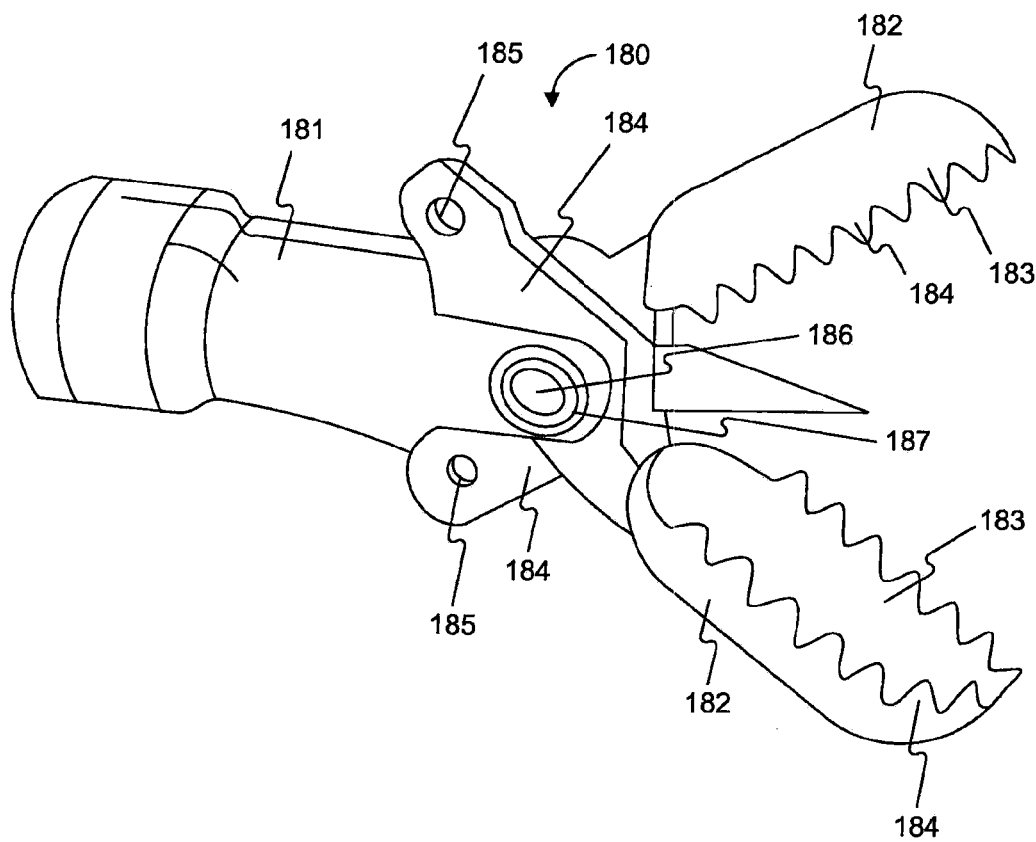
FIG. 6 is a perspective view of a jaw assembly of an endoscopic instrument according to an embodiment of the present invention.
Figure 7:
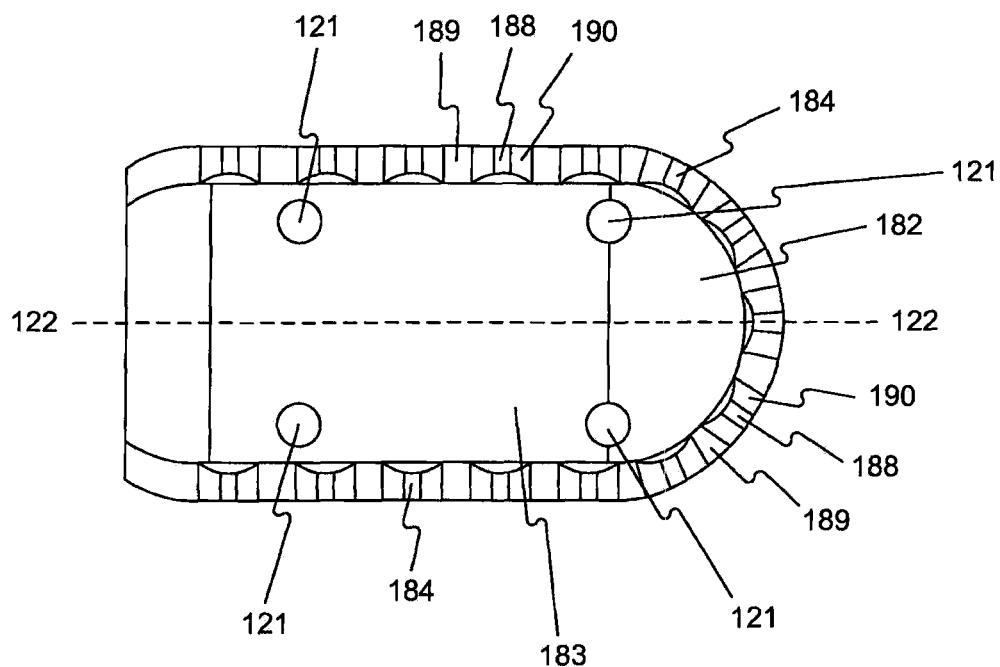
FIG. 7 is a view of a jaw portion of the jaw assembly of FIG. 6.
Figure 9:
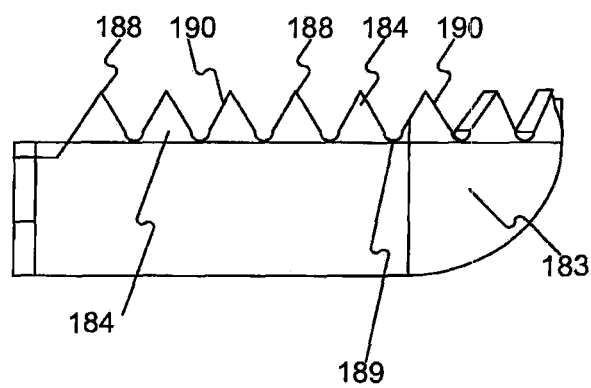
FIG. 9 is a side view of a jaw portion of the jaw assembly of FIG. 6.
Figure 10:
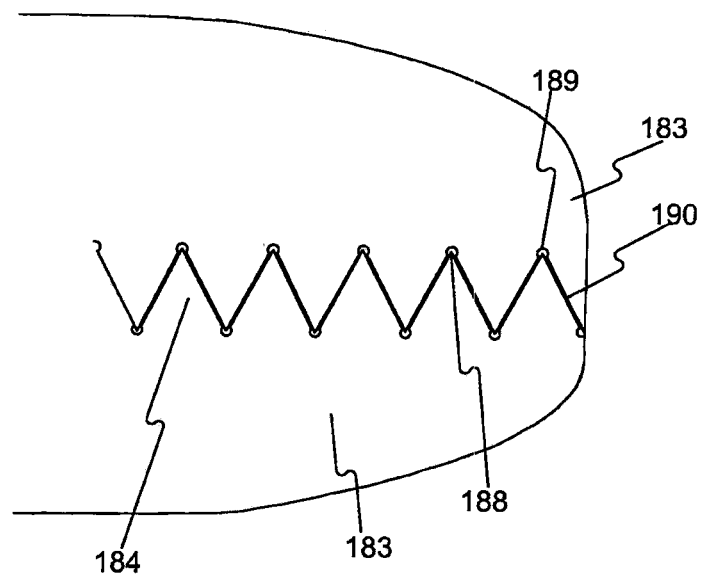
FIG. 10 is a side view of the mated jaw portions of FIG. 9.

Embodiments of the invention include a medical device having jaws with various tooth and/or teeth configurations that overcome one or more of the drawbacks. A jaw assembly 180 according to an exemplary embodiment of the invention is depicted in FIGS. 6, 7, and 9. The jaw assembly 180 includes a clevis 181 configured to be connected to the end of an elongate member 13. Opposing jaws 182 are rotatably attached to the distal end of the clevis 181. Each jaw 182 has a jaw portion 183 connected to a tang portion 184 with mounting holes 185 on the proximal end of the tang portion 184. The holes 185 may be configured to receive and/or retain a wire 15 or other interface device via the clevis 181. Each tang portion 184 also has an axle hole 186 configured to receive an axle 187 that may be connected to the clevis 181. Each jaw portion 183 has a plurality of teeth 184 configured to mate with the plurality of teeth 184 disposed on an opposing jaw portion 183. Material may be removed from the root 189 of adjoining teeth 184 so that, for example, sharper teeth (i.e., crest portions with smaller or no radii) may be used. As shown in FIG. 9, the root 189 has a circular cutout below the point where the crest 188 of an opposing jaw portion 183 would be captured, regardless of the sharpness of the crest 188 (i.e., the crest 188 may have a substantially zero radius). An example of such a configuration is depicted in FIG. 10. Accordingly, the crest 188 may be as sharp as desired, while still allowing the substantially diagonal portions 190 of opposing jaw portions 183 to come into contact with each other. Methods of sharpening teeth 184 such that the crest 188 has a substantially zero radius are known in the art (e.g., stamping, filing, casting). This jaw portion 183 configuration is advantageous as a sharper crest 188 results in a sharper tooth with an improved bite performance.

Figure 11:
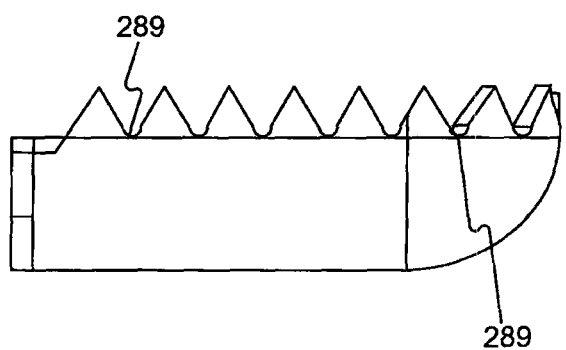
FIG. 11 is a side view of a jaw portion of an endoscopic instrument according to another embodiment of the present invention.
Figure 12:
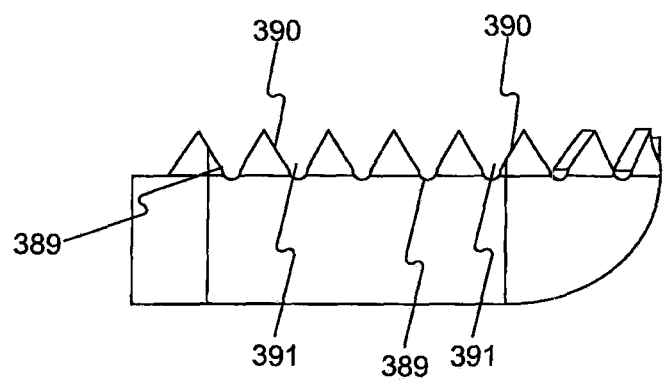
FIG. 12 is a side view of a jaw portion of an endoscopic instrument according to yet another embodiment of the present invention.

In various embodiments, the cutout portions of the root may have any shape or configuration that permits contact between substantially diagonal portions of opposing jaws that include sharp teeth. For example, FIG. 11 shows a root 289 configuration where the cutout is substantially U-shaped. In another example, FIG. 12 shows a root 389 configuration where the circular cutout is shifted vertically. Each root 389 has a center 391 that is disposed below the lower end of the substantially diagonal surfaces 390. In yet another example, the root portion and/or the circular cutout may also be shifted horizontally, so long as the substantially diagonal portions of the opposing jaw portions come into contact with each other without crests contacting the corresponding roots. In various embodiments, there may be a gap between the tip of the crest and the root, however, the tip of the crest may also just touch the lowest point of the root.

Figure 13:
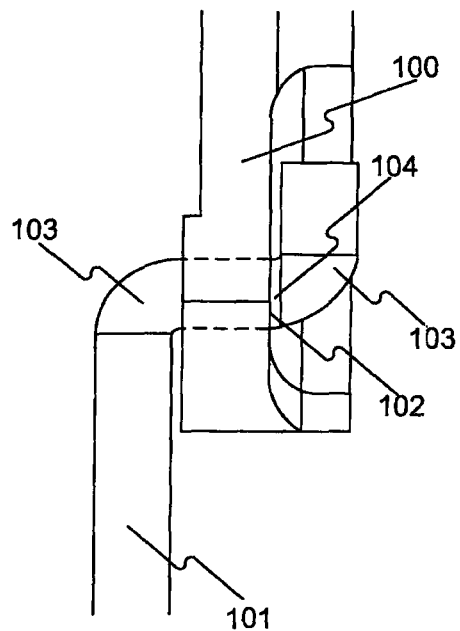
FIG. 13 is a top view of a tang portion and control wire of an endoscopic instrument.

FIG. 13 shows a profile of a tang portion 100 of an end effector assembly for a medical instrument, with a wire 101 disposed in a mounting hole 102 of the tang portion 100. The end portion of the wire 101 has a roughly Z-shaped configuration so as to lodge the wire 101 in the hole 102, allow the wire 101 to rotate with respect to the hole 102, and/or prevent the wire 101 from falling out of the hole 102. The wire end portion has two bends 103 with an interface portion 104 between the bends 103 that contacts the internal surface of the hole 100. The interface portion 104 has substantially the same length as the axial length of the hole 102 and/or the width of the tang 100, for example, to prevent the wire 101 from shifting in the hole 102 and/or falling out of the hole 102. Two methods of forming the roughly Z-shaped configuration (i.e., bends 103) include stamping and/or forging a straight wire 101 into the roughly Z-shaped configuration, however, any method known in the art may be used. If the Z-shape is formed by a stamping or forging operation, the minimum length of the interface portion 104 (i.e., the portion of the wire between the bends) that may be formed is about 0.015 inches.

Figure 14:
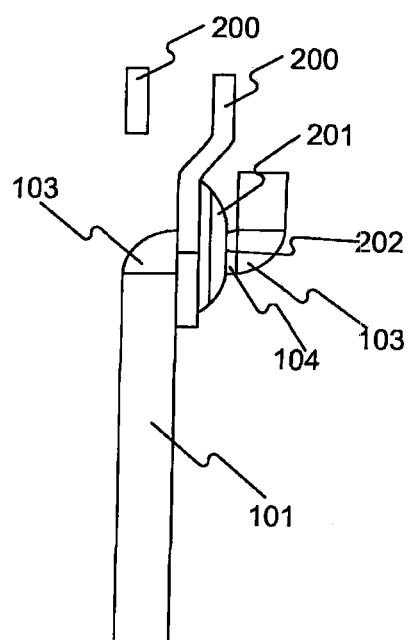
FIG. 14 is a top view of a tang portion and control wire of an endoscopic instrument according to an embodiment of the present invention.

Embodiments of the invention include a medical device having an end effector assembly with various tang configurations. In an exemplary embodiment of the invention, a substantially narrow tang portion may have a widened portion, for example, by placing a dimple 201 on a tang portion 200 around a mounting hole 202. For example, as shown in FIG. 14, the dimple 201 may extend from the surface of the tang portion 200 and increase the width of the tang portion 200. The dimple 201 may be stamped onto the tang portion 200 so as to increase the width of the tang portion 200. This is advantageous because it allows the tang portion 200 and/or the rest of the jaw assembly to have a smaller thickness while still allowing the jaw assembly to accommodate the end portion of the wire 101 set forth above.

Specifically, it allows the thickness of the tang portion 200 without the dimple 201 to be reduced, while still allowing the tang portion 200 and/or the mounting hole 202 to receive and accommodate an end portion of a wire 101 with an interface portion 104 having a length of about 0.015 inches. For example, if the width of the tang portion 200 is about 0.007 inches, a dimple 201 of about 0.008 inches could be added to the tang portion 200 so as to accommodate an end portion of a wire 101 with an interface portion 104 having a length of about 0.015 inches, without the end portion of the wire 101 undesirably shifting in and/or falling out of the mounting hole 202. This is especially advantageous when manufacturing a stamped jaw (with tang) having a thickness of material that is less than the length of the interface portion 104.

Figure 15A:
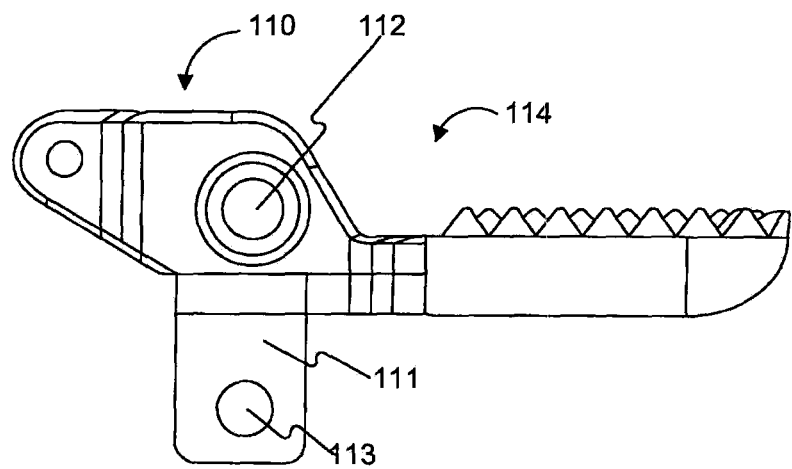
FIG. 15A is a side view of a jaw with a tang portion, having an unfolded additional section, of an endoscopic instrument according to another embodiment of the present invention.
Figure 15B:
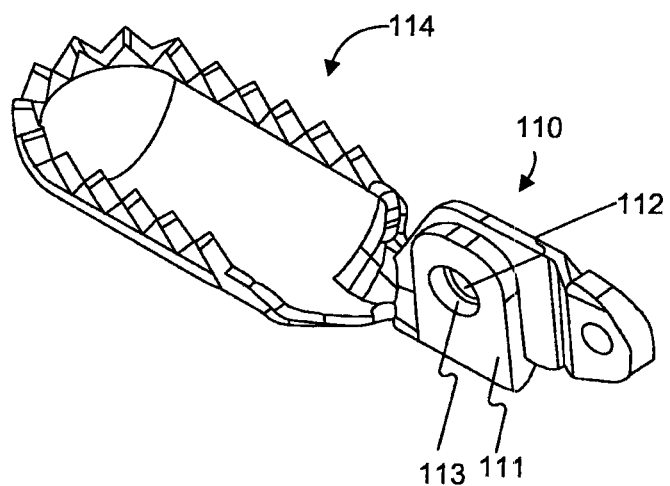
FIG. 15B is a perspective view of the jaw with the tang portion of FIG. 15A, with the additional section folded.

In various embodiments, the bends 103 need not make the end portion of the wire 101 into necessarily a roughly Z-shaped configuration. For example, the bends 103 could form the end portion of the wire 101 into a roughly U-shaped configuration. In addition, the bends 103 may be formed using any method known in the art. Furthermore, the dimples 201 may be formed using any method known in the art. For example, material may be soldered on and/or attached to the tang portion 200 using an adhesive to form dimples 201. Additionally, the thickness of the tang portion need not be increased by placing a dimple, as a portion of the tang portion may be folded over to increase the thickness. For example, in a tang portion manufactured from material having a thickness of about 0.007 inches, folding over the material would create a tang portion with a thickness of about 0.014 inches. FIGS. 15A and 15B described below illustrate this concept as it relates to the axle hole of the jaw. The dimple 201 and/or tang portion 200 may be of any desired shape, size, dimensions, and/or configurations. For example, all the dimensions listed above are exemplary only.

In an exemplary embodiment of the invention, a tang portion of an end effector assembly of a medical device may have a widened and/or thickened portion, for example, by folding over material in a portion of the tang around the axle hole.

As shown in FIGS. 15A-15B, a tang portion 110 of an end effector, such as a jaw 114, may be formed such that it has an additional portion 111 extending from the tang portion 110. The additional portion 111 has through hole 113 with substantially the same diameter as an axle hole 112 of the rest of the tang portion 110. The additional portion 111 may then be folded over such that the through hole 113 is aligned with the axle hole 112. For example, a tang portion 110 may be stamped from a material having a thickness of about 0.007 inches. Thus, both the tang portion 110 and the additional portion 111 have a width of about 0.007 inches. When folded over, the combined width of the tang portion 110 and the additional portion 111 becomes about 0.014 inches. A wider tang portion 110, and particularly a longer axle hole (the combined holes 112 and 113), may be advantageous because it imparts a wider footprint to the jaw mechanism, which may increase the stability and/or precision of the jaw, for example, during the clamping of opposing jaws.

In various embodiments, the tang portion may be widened by forming and then folding over multiple additional portions, for example, three additional portions. The width and/or thickness of other portions of a medical device, including other portions of the end effectors and/or end effector assembly, may be increased using this method. The folded over portion and/or tang portion may be of any desired shape, size, dimensions, and/or configurations. For example, all the dimensions listed above are exemplary only.

Embodiments of the invention include a medical device with holes in various portions of the medical device, including through the end effectors. For example, as shown in FIG. 7, a jaw 82 of a jaw assembly may have fenestration holes 121 in different portions of jaw 82. Fenestration holes 121 may assist in removing biopsy samples from the jaw 82, for example, by allowing fluid to enter the jaw 82 through the fenestration holes 121, flow between the biopsy sample and the jaw 82, and thus allow the biopsy sample to be flushed out of the jaw 82. The fenestration holes 121 may be disposed off a centerline 122 of the jaw 82. This may be advantageous as when the jaw 82 is placed down a channel, for example the working channel of an endoscope, because the jaw 82 may contact the inner wall of the channel substantially along its centerline 122, the channel will not come into contact with the fenestration holes 121. This may be desirable, for example, because contact between the holes 121 and the channel may cause the holes 121 to catch portions of the channel. This may cause damage to the channel and/or prevent the movement of the medical device with respect to the channel.

In various embodiments, the holes 121 may have any shape, for example, round, circular, oblong, square, and triangular. The holes 121 may also have of any size and have any desired dimensions. There may be any number of holes 121 on any portion of the medical device, but what is disclosed here are holes 121 that are not substantially located on the centerline 122 of the medical device and/or portions of the medical device that may come into contact with a channel and/or another object external to the medical device. The holes 121 need not necessarily be on portions of the medical device that completely preclude the holes 121 from coming into contact with the channel and/or another object external to the medical device, but may be on a portion where such contact is reduced or minimal relative to other portions of the medical device.

Figure 16:
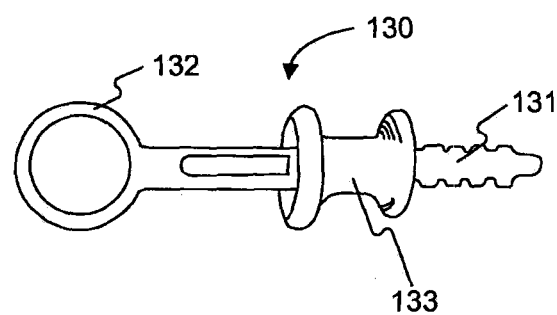
FIG. 16 is a side view of a handle of an endoscopic instrument according to an embodiment of the present invention.
Figure 17:
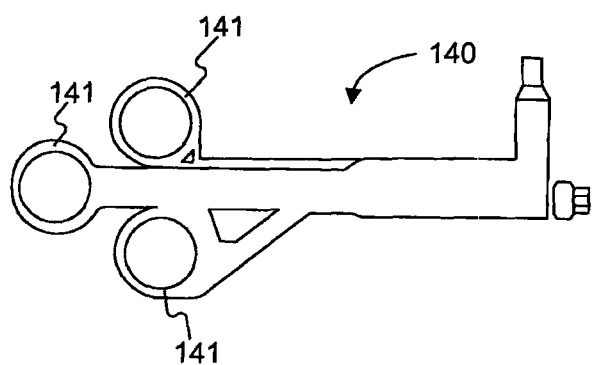
FIG. 17 is a side view of a handle of an endoscopic instrument according to another embodiment of the present invention.

Embodiments of the invention include a medical device with user-interface portions configured to reduce stress (i.e. force) on the operator. For example, the handle of a medical device (e.g., an endoscopic instrument with a handle portion) may have soft-grip features. The entire handle may comprise the soft-grip features, or portions of the handle may have soft grip features, for example, those portions that accommodate a user's fingers. For example, in a handle 130 comprising a ring portion 132, an elongate portion 131, and a spool portion 133 disposed around the elongate portion 131, as shown in FIG. 16, the soft-grip features may be incorporated into the ring portion 132 and/or the spool portion 133. In another example, in a handle 140 comprising three-rings 141, as shown in FIG. 17, the soft-grip features may be incorporated into one or more of the three rings 141.

The soft-grip feature may be a low durometer material, for example, santoprene or urethane, incorporated into the medical device. The soft-grip features reduce stress on the operator, for example, by reducing the stress on their hands, and have a more comfortable ergonomic feel. The reduction in stress on the user may allow the user to perform more procedures than with a medical device without the soft-grip features.

In various embodiments, any soft material may be used as soft-grip features, for example, rubber and/or rubbery thermoplastics. The soft-grip features may be placed on any portion of the medical device, for example, that have the potential to be handled by a user, provided that it does not otherwise interfere with the operation of the medical device. The soft-grip features may also be varied across portions of the device. For example, portions of the device may have different materials with different durometers.

Embodiments of the invention include a medical device having portions with variable stiffness. For example, in endoscopic instruments with an elongate member, portions of the elongate member may have variable stiffness. Some portions of the elongate member may be more flexible, for example, to allow the elongate member to be navigated through areas of the body having curves (i.e., tubular regions with greater tortuosity). Because of the flexibility, at least these portions of the elongate member may easily bend around even sharp curves, for example, in the gastrointestinal tract. Other portions of the elongate member may be more rigid, for example, to allow the elongate member to be properly advanced through areas of the body (e.g., tubular regions). Because of the rigidity, at least these portions of the elongate member can be pushed through, for example, the gastrointestinal tract.

Figure 4:
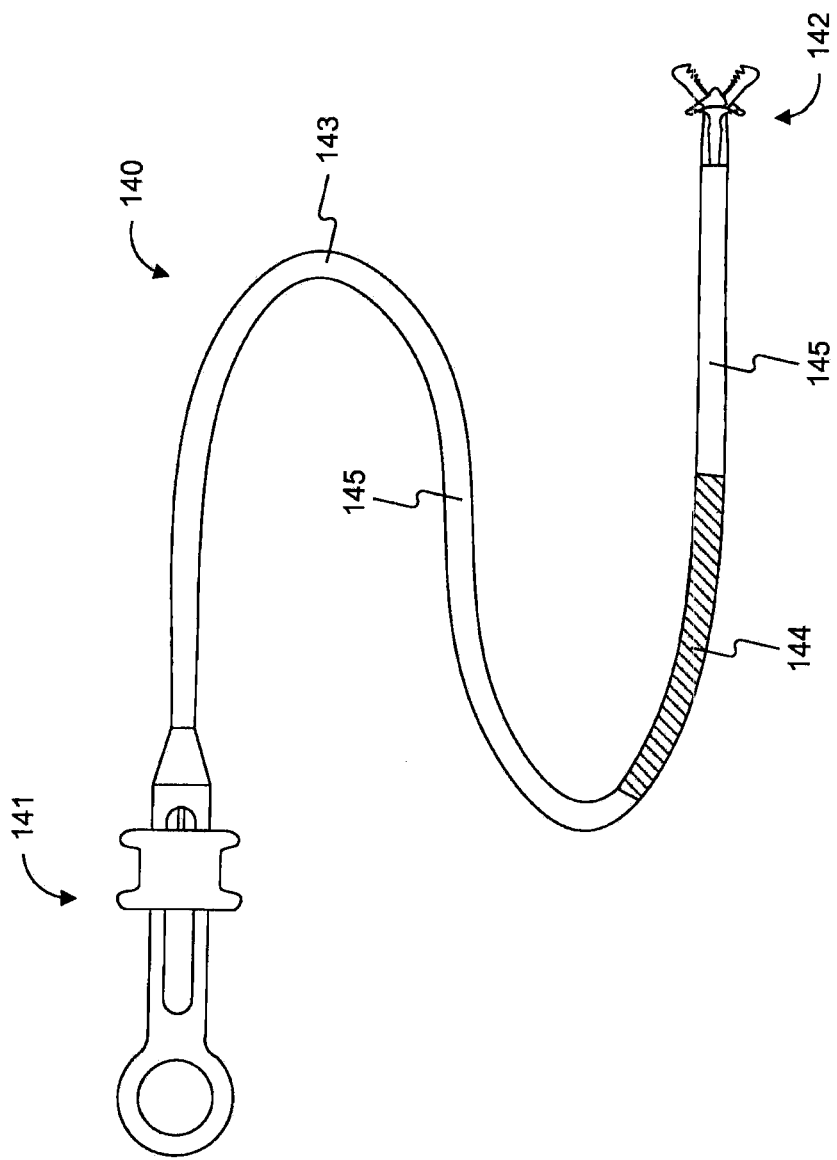
FIG. 4 is a schematic view of an endoscopic instrument with an elongate member of variable flexibility according to an embodiment of the present invention.

In an exemplary embodiment of the present invention, FIG. 4 shows an endoscopic instrument 140 with a handle 141 and an end effector assembly 142 connected by an elongate member 143. The elongate member 143 may have a diameter of about 2.4 mm and a length of about 350 cm. However, any other dimensions suitable for its intended use are also possible. The entire elongate member 143 has a constant strength and feel from its proximal end to distal end, however, a portion 144 of the distal third of the elongate member 143 proximal to the distal end effector assembly has a lower stiffness than the other portions 145 of the elongate member 143. Methods of reducing the stiffness of the desired portion 144 of the elongate member 143 include reducing the diameter of the elongate member 143 in the targeted area, and/or varying the material used in the elongate member 143 such that the lower stiffness portion 144 is comprised of a more flexible material than the higher stiffness portions 145.

In various embodiments, the elongate member may have its rigidity varied along any portion of the elongate member, may have multiple portions with multiple levels of stiffness, and/or may be manufactured using any method known in the art.

In various embodiments, all aspects of the invention set forth herein may be used in conjunction with any medical device, instrument, or procedure, and/or any non-medical device, instrument, or procedure. In addition, one or more of the aspects of the invention set forth herein may be combined in the same device.

Other embodiments of the invention will-be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device comprising:
   a handle;
   an end effector assembly; and
   a member connecting the handle to the end effector assembly,
   wherein the end effector assembly comprises opposing jaw portions each including a plurality of teeth,
   wherein each of the teeth includes a crest, a root, a first intermediate portion between the crest and the root, and a second intermediate portion between the crest and a root of an adjoining tooth, and
   wherein surfaces of first intermediate portions and surfaces of second intermediate portions of opposing as portions are configured to contact each other when the opposing jaw portions are fully closed, wherein the surfaces of the first intermediate portion and the second intermediate portion of a tooth are transverse to a longitudinal axis of the jaw portions with no portion of the surfaces of the first intermediate portion and the second intermediate portion of the tooth being aligned, and
   wherein the root has a recessed portion configured to accommodate a sharp, pointed tip of the crest of an opposing tooth,
   wherein a gap exists between the tip and the lowest point of the root of an opposing tooth when the opposing jaw portions are filly closed.

2. The medical device of claim 1, wherein at least one opposing jaw portion has a tissue receiving portion configured to retain at least one tissue sample, the tissue receiving portion defining at least one hole configured so as to, substantially prevent contact between an outer edge of the hole and a tube-like member in which the end effector assembly is configured to extend through.

3. The medical device of claim 1, wherein the handle is a soft-grip handle.

4. A medical device comprising:
   a handle;
   an end effector assembly; and
   a member connecting the handle to the end effector assembly,
   wherein the end effector assembly comprises opposing jaw portions each including plurality of teeth,
   wherein each of the teeth includes a crest, a root, a first intermediate portion between the crest and the root, and a second intermediate portion between the crest and root of an adjoining tooth, and
   wherein surfaces of first intermediate portions and surfaces of second intermediate portions of opposing jaw portions are configured to contact each other When the opposing jaw portions are fully closed, wherein the surfaces of the first intermediate portion and the second intermediate portion of a tooth are transverse to a longitudinal axis of the jaw portions portion of the surfaces of the first intermediate portion and the second intermediate portion of the tooth being aligned,
   wherein the root has a recessed portion configured to accommodate a sharp, pointed tip of the crest of an opposing tooth, and
   wherein a gap exists between the tip and the lowest point of the root of an opposing tooth when the opposing jaw portions are fully closed,
   wherein the root is at least a partial, substantially circular cutout.

5. The medical device of claim 4, wherein a center of the cutout is displaced vertically relative to adjacent intermediate portions.

6. The medical device of claim 4, wherein a center of the cutout is displaced horizontally relative to a center of adjacent intermediate portions.

7. A medical device comprising:
   a handle;
   an end effector assembly; and a member connecting the handle to the end effector assembly,
wherein the end effector assembly comprises opposing jaw portions each including a plurality of teeth,
wherein each of the teeth includes a crest, a root, a first intermediate portion between the crest and the root, and a second intermediate portion between the crest and the root of an adjoining tooth, and
wherein surfaces of first intermediate portions and surfaces of second intermediate portions of opposing jaw portions are configured to contact each other when the opposing jaw portions are fully closed, wherein the surfaces of the first intermediate portion and the second intermediate portion of a tooth are transverse to a longitudinal axis of the jaw portions with no portion of the surfaces of the first intermediate portion and the second intermediate portion of the tooth being aligned,
wherein the root has a recessed portion configured to accommodate a sharp, pointed tip of the crest of an opposing tooth, and
wherein a gap exists between the tip and the lowest point of the root of an opposing tooth when the opposing jaw portions are fully closed,
wherein the root is a U-shaped groove.

8. The medical device of claim 7, wherein a center of the U-shaped groove is displaced vertically relative to adjacent intermediate portions.

9. The medical device of claim 7, wherein a center of the U-shaped groove is displaced horizontally relative to a center of adjacent intermediate portions.

10. A medical device comprising:
a handle;
an end effector assembly; and
a member connecting the handle to the end effector assembly,
wherein the end effector assembly comprises opposing jaw portions each including a plurality of teeth,
wherein each of the teeth includes a crest, a root, a first intermediate portion between the crest and the root, and a second intermediate portion between the crest and a root of an adjoining tooth, and
wherein surfaces of first intermediate portions and surfaces of second intermediate portions of opposing jaw portions are configured to contact each other when the opposing jaw portions are fully closed, wherein the surfaces of the first intermediate portion and the second intermediate portion of a tooth are transverse to a longitudinal axis of the jaw portions with no portion of the surfaces of the first intermediate portion and the second intermediate portion of the tooth being aligned,
wherein the root has a recessed portion configured to accommodate a sharp, pointed tip of the crest of an opposing tooth, and
wherein a gap exists between the tip and the lowest point of the root of an opposing tooth when the opposing jaw portions are fully closed,
wherein each opposing jaw portion includes a tang defining a mounting hole configured to receive one of a wire and an axle, and
wherein the tang includes a portion disposed around the mounting hole that has a thickness greater than a thickness of other portions of the tang,
wherein a section of the tang defining a through hole is folded so that the through hole is substantially aligned with the mounting hole.

11. A medical device comprising:
a handle;
an end effector assembly; and
an elongate, flexible member connecting the handle to the end effector assembly,
wherein the end effector assembly includes a pair of opposing biopsy jaws having teeth for cutting a tissue sample, the pair of opposing biopsy jaws each having a tissue receiving portion other than teeth having roughened inner and outer surfaces, and at least one of the pair of opposing biopsy jaws defining a hole, the bole configured so as to substantially prevent contact between an outer edge of the hole and a tube-like member in which the end effector assembly is configured to extend through,
wherein each biopsy jaw further includes a tang defining a mounting hole configured, to receive one of a wire and an axle, the tang including a portion disposed around the mounting hole that has a thickness greater than a thickness of other portions of the tang,
wherein each biopsy jaw further includes a plurality of teeth, each of the teeth including a crest, a root, a first intermediate portion between the crest and the root, and a second intermediate portion between the crest and a root of an adjoining tooth,
wherein surfaces of first intermediate portions and surfaces of second intermediate portions of opposing biopsy jaws are configured to contact each other when the biopsy jaws are fully closed, wherein the surfaces of the first intermediate portion and the second intermediate portion of a tooth are transverse to a longitudinal axis of the jaw portions with no portion of the surfaces of the first intermediate portion and the second intermediate portion being aligned, and the root has a recessed portion configured to accommodate a sharp pointed tip of the crest, and
wherein a gap exists between the tip and the lowest point of the root of an opposing tooth when the opposing jaw portions are fully closed.

12. The medical device of claim 11, wherein the biopsy jaw includes a jaw extending from an arm, and
wherein all edges of the jaw other than a cutting edge of the jaw are non-sharp.

13. The medial device claim 11, wherein the roughened surface is formed by one of grit blasting, media tumbling, plating, sputtering, photo-etching, acid-etching and plasma coating.

14. The medical device of claim 11, wherein the handle is a soft-grip handle.

15. A medical device comprising:
a handle;
an end effector assembly: and
an elongate, flexible member connecting the handle to the end effector assembly,
wherein the end effector assembly includes a pair of opposing biopsy jaws each having a tissue receiving portion other than teeth having a roughened surface, and at least one of the pair of opposing biopsy jaws defining a hole, the hole configured so as to substantially prevent contact between an outer edge of the hole and a tube-like member in which the end effector assembly is configured to extend through,
wherein each biopsy jaw further includes a tang defining a mounting hole configured to receive one of a wire and an axle, the tang including a portion disposed around the mounting hole that has a thickness greater than a thickness of other portions of the tang, wherein each biopsy jaw further includes a plurality of teeth, each of the teeth including a crest, a root, a first intermediate portion between the crest and the root, and a second intermediate portion between the rest and a root of an adjoining tooth, wherein surfaces of first intermediate portions and surfaces of second intermediate portions of opposing biopsy jaws are configured to contact each other when the biopsy jaws are fully closed, wherein the surfaces of the first intermediate portion and the second intermediate portion of a tooth are transverse to a longitudinal axis of the jaw portions with no portion of the surfaces of the first intermediate portion and the second intermediate portion of the tooth being aligned, and the root has a recessed portion configured to accommodate a sharp, pointed tip of the crest.

wherein a gap exists between the tip and the lowest point of the root of an opposing tooth when the opposing jaw portions are fully closed, wherein a section of the tang defining a through hole is folded so that the through hole is substantially aligned with the mounting hole.

\* \* \* \* \*

UNITED STATES PATENT AND TRADEMARK OFFICE
CERTIFICATE OF CORRECTION

PATENT NO. : 8,469,993 B2
APPLICATION NO. : 10/778226
DATED : June 25, 2013
INVENTOR(S) : Elliott Rothberg et al.

It is certified that error appears in the above-identified patent and that said Letters Patent is hereby corrected as shown below:

In the Claims
Claim 1, Col. 12, Line 8, "as" should read --jaw--.
Claim 4, Col. 12, Line 44, "When" should read --when--.
Claim 4, Col. 12, Line 48, "portions portion" should read --portions with no portion--.
Claim 15, Col. 15, Line 9, "arc" should read --are--.

Signed and Sealed this
Twentieth Day of August, 2013

Teresa Stanek Rea
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 8,469,993 B2 | Page 1 of 1 |
| APPLICATION NO. | : 10/778226 | |
| DATED | : June 25, 2013 | |
| INVENTOR(S) | : Rothberg et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1498 days.

Signed and Sealed this
Thirtieth Day of December, 2014

Michelle K. Lee
*Deputy Director of the United States Patent and Trademark Office*